US008457755B2

(12) United States Patent
Snitting

(10) Patent No.: US 8,457,755 B2
(45) Date of Patent: Jun. 4, 2013

(54) CONTAINER FOR STORING AN IMPLANTABLE MEDICAL DEVICE AND A METHOD FOR PACKAGING SUCH A DEVICE

(75) Inventor: Tomas Snitting, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 130 days.

(21) Appl. No.: 12/531,593

(22) PCT Filed: Apr. 24, 2007

(86) PCT No.: PCT/SE2007/000397
§ 371 (c)(1),
(2), (4) Date: Sep. 16, 2009

(87) PCT Pub. No.: WO2008/130292
PCT Pub. Date: Oct. 30, 2008

(65) Prior Publication Data
US 2010/0114247 A1 May 6, 2010

(51) Int. Cl.
*A61N 1/00* (2006.01)
*A61B 17/06* (2006.01)

(52) U.S. Cl.
USPC ............................................. 607/60; 206/438

(58) Field of Classification Search
USPC .................. 607/60, 36; 206/438; 455/91–107
See application file for complete search history.

(56) References Cited

U.S. PATENT DOCUMENTS

| 4,830,005 | A | 5/1989 | Woskow | |
|---|---|---|---|---|
| 5,861,019 | A | 1/1999 | Sun et al. | |
| 6,292,697 | B1 | 9/2001 | Roberts | |
| 7,637,868 | B2 * | 12/2009 | Saint et al. | 600/365 |
| 7,720,544 | B2 * | 5/2010 | Christman et al. | 607/60 |
| 2002/0117408 | A1 * | 8/2002 | Solosko et al. | 206/210 |
| 2002/0147388 | A1 | 10/2002 | Mass et al. | |
| 2003/0025645 | A1 | 2/2003 | Amundson et al. | |
| 2005/0154428 | A1 | 7/2005 | Bruinsma | |
| 2005/0275591 | A1 | 12/2005 | King et al. | |
| 2006/0020300 | A1 | 1/2006 | Nghiem et al. | |
| 2006/0045543 | A1 * | 3/2006 | Kato et al. | 399/1 |
| 2006/0197494 | A1 | 9/2006 | Schommer | |
| 2006/0224206 | A1 | 10/2006 | Dublin et al. | |
| 2006/0247712 | A1 | 11/2006 | Fuller et al. | |
| 2006/0250314 | A1 | 11/2006 | Forster et al. | |
| 2007/0052613 | A1 | 3/2007 | Gallschuetz et al. | |
| 2007/0119741 | A1 * | 5/2007 | Wenger et al. | 206/438 |
| 2008/0146871 | A1 * | 6/2008 | Arneson et al. | 600/101 |
| 2008/0185312 | A1 * | 8/2008 | Geurts et al. | 206/525 |
| 2009/0105597 | A1 * | 4/2009 | Abraham | 600/466 |
| 2009/0240309 | A1 * | 9/2009 | Rahman | 607/60 |

* cited by examiner

*Primary Examiner* — Christopher D Koharski
*Assistant Examiner* — Catherine Voorhees

(57) ABSTRACT

An implantable medical device is stored in a container prior to implantation in body tissue. The IMD includes transmitter/receiver circuitry and at least one antenna. The storage container (packaging) includes an impedance altering substance positioned in proximity to the IMD when stored in the container, the substance having electrical material properties that alter the input impedance of the antenna to improve the reception and transmission properties of the antenna when the IMD is stored in the container. A container for storing an IMD having an antenna has a packaging tray for housing the IMD, the packaging tray having a support for supporting the IMD and the container including a substance positioned in proximity to the support that has electrical material properties that after the input impedance of the antenna of the IMD supported by the support, so as to improve the reception and transmission properties of the antenna. A method for packaging an IMD prior to implantation in body tissue includes the step of providing such an impedance altering substance in the pre-implantation IMD packaging, in proximity to the packaged IMD.

48 Claims, 4 Drawing Sheets

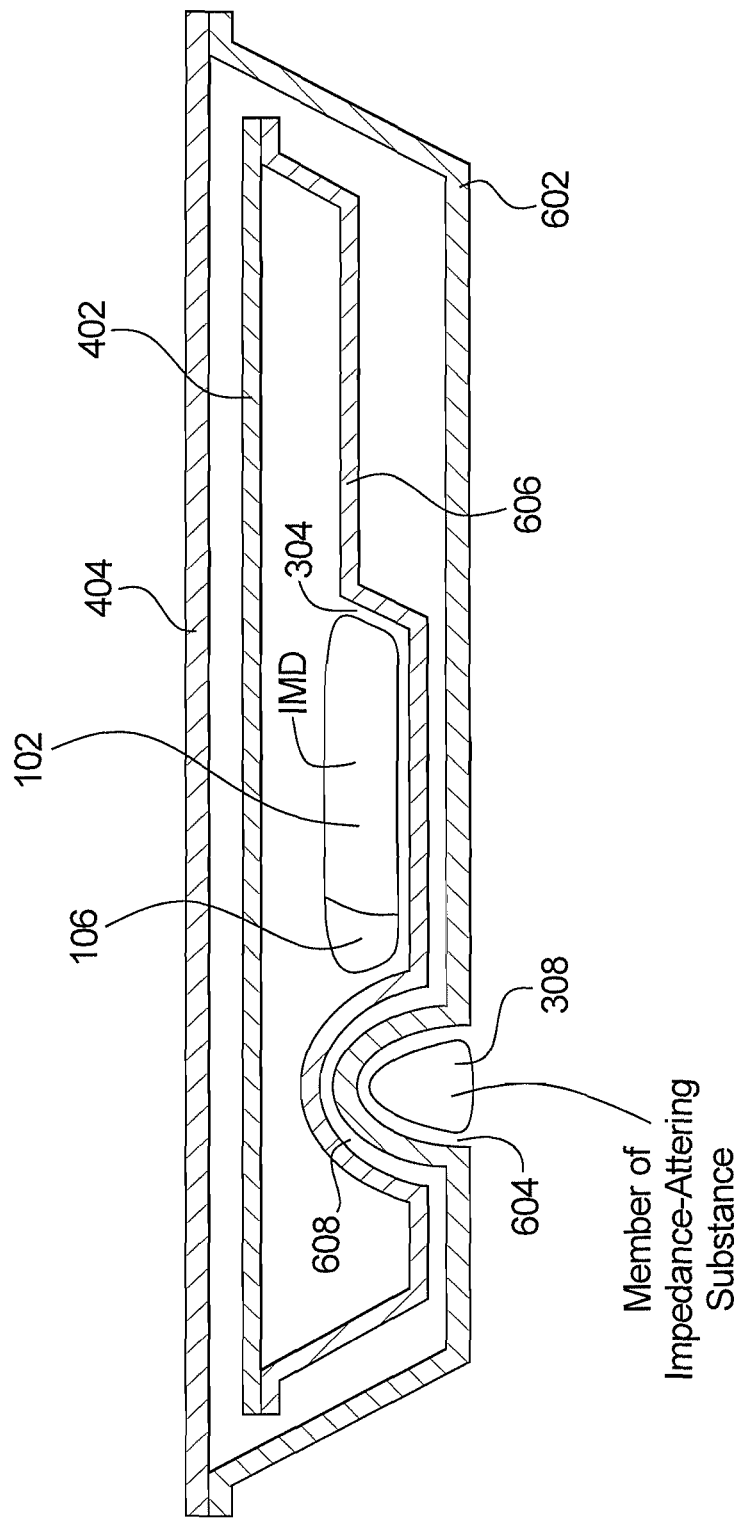

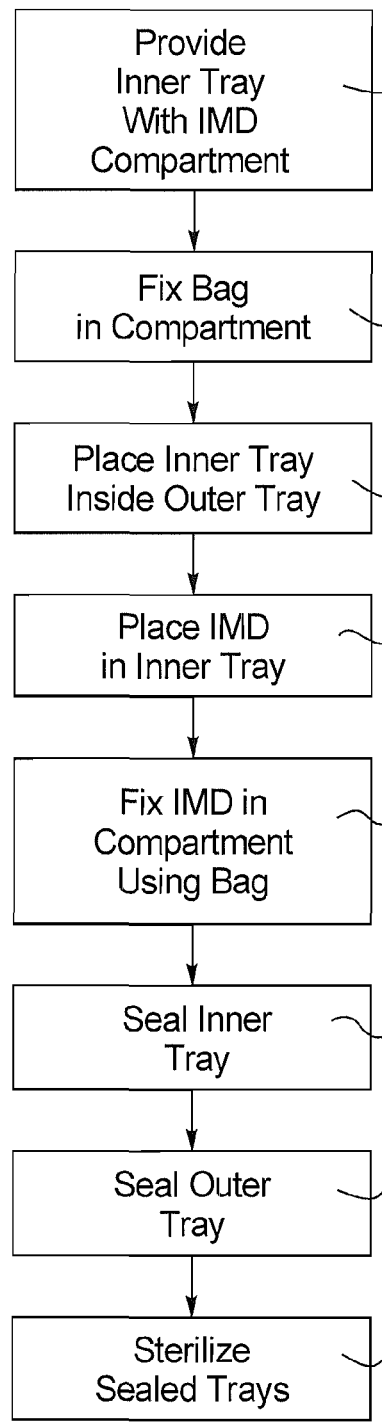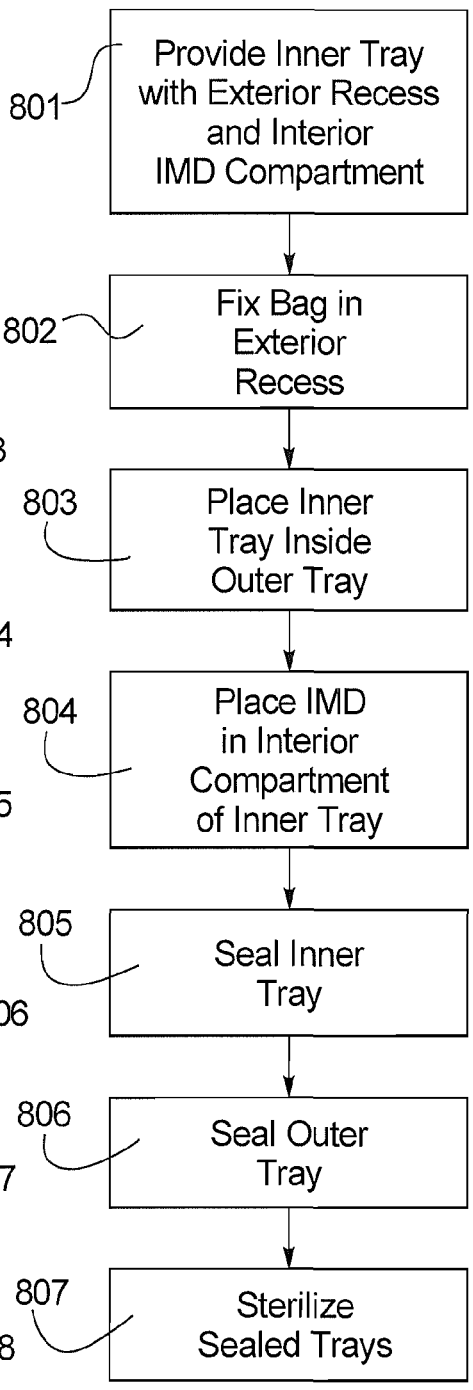

CONTAINER FOR STORING AN IMPLANTABLE MEDICAL DEVICE AND A METHOD FOR PACKAGING SUCH A DEVICE

BACKGROUND OF THE INVENTION

1. Field of the Invention

The present invention relates to a system for improving the communication with an implantable medical device while being stored prior to implantation in body tissue. The present invention also relates to an apparatus comprising an implantable medical device and a container for storing the implantable medical device prior to implantation in body tissue. Further, the present invention relates to a container for storing an implantable medical device. Finally, the present invention relates to a method for packaging an implantable medical device prior to implantation in body tissue.

2. Description of the Prior Art

In the context of implantable medical devices, IMDs, it is common to provide a communication link between the implanted IMD and an external device, such as a programmer or monitor, in order to allow for transmission of commands from the external device to the implanted IMD and to allow for transmission of stored information and/or sensed physiological parameters from the implanted IMD to the external device. Conventionally, communication between an implanted IMD and an external device has been accomplished by means of a telemetry system which includes a radio transmitter/receiver and one or more antennas included in the IMD and a radio transmitter/receiver and one or more antennas included in the external device. The IMD typically includes an antenna located either within the hermetic housing containing the circuitry, in a plastic header or connector block used to interconnect the IMD to electrical leads. Telemetry is a technology that allows the remote measurement and reporting of information of interest to the system operator. In the context of IMDs, the IMD is arranged to measure and record data regarding the patient and to transmit these data to the programmer, typically via wireless communications using radio frequency systems. By means of telemetry the programmer can run tests, and program and operate the IMD at a distance from the patient.

In the past, the external device has been provided with a programming head containing an antenna, intended to be placed in close proximity to the implanted IMD. Today, telemetry systems for IMDs have been proposed, in which to the communication occurs directly between the external device, e.g. the programmer or monitor, which may be located at a distance from the patient, and the implanted IMD.

IMD telemetry systems are generally designed for maximum efficiency under implanted condition, i.e. the dielectric constant and conductivity of body tissue is taken into account when designing the telemetry and antenna system. Programming and interrogation operations, however, are not limited to occur when the IMD has been implanted. When the IMD is stored before the implant procedure and during the implant procedure, telemetry communication may be required for testing procedures or for verifying or customizing initial programmable parameter values before the IMD is implanted. However, since IMD telemetry systems are not designed for conditions where the IMD is located outside the implanted environment prior to implantation, the efficiency of the IMD telemetry systems prior to implantation is affected.

United States Patent Application Publication No. 2006/0020300 A1 discloses a solution to this problem. A wireless communication system is described, comprising an IMD and a package antenna adapted for coupling to the IMD antenna when the IMD is outside the implanted environment. The package antenna extends the IMD antenna length prior to implantation in order to improve the efficiency of the telemetry link between the IMD and an external device, such as a programmer or monitor. The package antenna is provided on a pouch in which the IMD is placed, or is provided on the packaging tray assembly, e.g. placed within the packaging tray or on the tray lid. The package antenna is made of a conductive material and is in the form of a monopole, dipole, loop, microstrip patch, or slot antenna.

However, the use of a conductive material formed into an antenna, as suggested by United States Patent Application Publication No. 2006/0020300 A1, is somewhat complicated and thus connected with costs. The capacitive or direct to electrical coupling between the packaging antenna and the IMD is a weak link, due to the risk of interruption of the coupling.

United States Patent Application Publication No. 2006/0224206 A1 discloses an IMD outfitted with an optional antenna assembly. However, this optional antenna assembly is optimized to suit the need of the particular IMD is application under implanted conditions, e.g., in consideration of the age, sex, size, or condition of the patient, or implant orientation within the patient, and not under conditions prior to implantation.

United States Patent Application Publication No. 2006/0197494 A1 describes a shipping container for storing an IMD prior to implantation. However, this shipping container is designed to allow charging of the IMD without disturbing the container, and not designed to increase the efficiency of the IMD telemetry system.

SUMMARY OF THE INVENTION

The above object is achieved in accordance with the present invention by an apparatus that includes an implantable medical device and a container for the implantable medical device prior to implantation, wherein the container has an impedance altering substance located therein in proximity to the antenna of the implantable medical device in the container, the impedance altering substance passively altering the input impedance of the antenna to improve the reception and transmission properties thereof while the implantable medical device is in the container.

The above object also is achieved in accordance with the present invention by a container having an impedance altering substance therein as described above, as well as by a method for packaging an implantable medical device prior to implantation that includes the step of providing such an impedance altering substance in the pre-implantation implantable medical device packaging, in proximity to the packaged implantable medical device.

For efficient transfer of energy, the impedance of the radio/transceiver, of the antenna and of the transmission line connecting them must be the same. Transceivers and their transmission lines are typically designed for 50Ω impedance. If the antenna has an impedance different from 50Ω, then there is a mismatch and an impedance matching circuit is required. The input impedance of an antenna is generally a function of frequency. Thus, the antenna will be matched to the interconnected transmission line and other associated equipment, such as a radio frequency transmitter/receiver or transceiver, only within a bandwidth. In addition, the input impedance of the antenna depends on many factors including its geometry, its method of excitation, and its environment, such as its proximity to surrounding objects, e.g. metal or dielectric objects.

In order to match the antenna to the radio and the transmission line of an IMD, tuning using tunable reactive components is possible and widens the usable spectrum of antenna impedances. However, the great difference between the environment of body tissue, where the IMD is implanted, and the environment of a shipping container, where the IMP is stored prior to implantation, would necessitate a very big tuning capability to handle this load. The present invention is based on the insight that a more viable way is to manipulate the input impedance of the antenna when the IMD is stored in the shipping container. By altering the electrical material properties of the storage packaging in the surroundings of the implantable medical device in accordance with the present invention, such that the input impedance of the antenna is adjusted to improve receive and transmit properties of the antenna when the implantable medical device is stored by the storage packaging, an effective improvement of the telemetry communication between an external device and the IMD is attained. This solution is uncomplicated and inexpensive. Since this solution does not require a capacitive or direct electrical coupling between the IMD and any external equipment in order to improve the efficiency of the antenna, the risk of interruption of such a coupling is eliminated.

The present invention makes it possible to efficiently communicate with the IMD while stored in a shipping container via radio frequency communication over larger distances. This enables a user to make an inventory of the IMDs in stock by means of an external radio frequency communication device, e.g., an inventory of the amount of IMDs, types of IMDs etc. The present invention also makes it possible for the user to execute testing procedures while the IMD is stored in the shipping container and while being in stock (inventory), or to verify or customize initial programmable parameter values before the IMD is implanted.

According to an advantageous embodiment of the system according to the present invention, the impedance altering substance sets the electrical material properties of a region in proximity to the antenna of the implantable medical device.

According to further advantageous embodiments of the system according to the present invention, the impedance altering substance sets the dielectric constant of the region above 10, and further advantageously sets the dielectric constant of the region between 10 and 60, preferably between 30 and 40. Advantageously, the impedance altering substance sets the conductivity of the region.

According to another advantageous embodiment of the system according to the present invention, the impedance altering substance mechanically fixes the implantable medical device in its position within the storage packaging, so the impedance altering substance provides a dual functionality.

According yet another advantageous embodiment of the system according to the present invention, the impedance altering substance is in the form of a member or component. Advantageously, the wireless communication circuit includes transmitter/receiver circuitry, and further advantageously, the storage packaging is in the form of a container as disclosed below.

The antenna of the IMD can be located in the housing of the IMD containing the device circuitry, in or on the plastic header of the IMD used to interconnect the IMD to electrical leads, mounted to the IMD housing, or incorporated as a portion of one of the leads. According to an advantageous embodiment of the apparatus according to the present invention, the member is positioned in the close surroundings of the antenna of the IMD, which efficiently influences the input impedance of the antenna more, and advantageously, the member extends along a substantial portion of the length of the antenna, which provides an even more effective influence on the input impedance of the antenna. The member can abut the IMD or be position with a small distance to the IMD. Advantageously, the member should not enclose too much of the antenna in order to avoid attenuation of the electromagnetic waves to and from the antenna.

Advantageously, the member of the apparatus of the present invention contains dielectric material in which conduction of electric current does not take place or is negligible, and in which an electric field can be maintained with a minimum loss of energy. Examples of dielectric materials are porcelain, ceramics, glass, and polymers. The member can have several different designs. The member can be in the form of a bag filled with a fluid and/or an amount of solids. The bag can for example be made of a polymeric material and be filled with any kind of fluid, such as a liquid or gel, or filled with an amount of solids made of ceramics, e.g. The member can also be in the form of one solid, e.g., made of ceramics. Advantageously, the dielectric constant of the member material is above 10. Further advantageously, the dielectric constant of the member material is between 10 and 60, preferably between 30 and 40. Advantageously, the conductivity of the member material is also set to efficiently influence the input impedance of the antenna.

Further advantageously, the member is made of a recyclable material, such as a polymer. If the member is in the form of a bag, the bag can be made of a polymeric material filed with a recyclable gel. Hereby, the container provided with the member is easy to recycle, since the container and member consist of only cardboard and plastics. If the container is equipped with a package antenna is made of metal as suggested by United States Patent Application Publication No. 2006/0020300 A1, the recycling process is more complicated since the antenna has to be separated from the rest of the container.

The support of the packaging tray is the designed location for the IMD within the packaging tray, and can have many different kinds of designs. The support can be in the form of a surface on which the front or rear side of the IMD is supported. The support can also be in the form of supporting members which press against the edges of the IMD and keeps it in position. In most cases, the support is formed as a recess having a shape that is complementary to the shape of the IMD.

According to an advantageous embodiment of the container according to the present invention, the support has such a configuration that the antenna of a stored implantable medical device is positioned in close proximity to the member.

BRIEF DESCRIPTION OF THE DRAWINGS

FIG. 6 is a cross-sectional side view of a third embodiment of the apparatus according to the present invention.

FIG. 7A is a schematic flowchart illustrating a first embodiment of the method according to the present invention.

FIG. 7B is a schematic flowchart illustrating a second embodiment of the method according to the present invention.

DESCRIPTION OF THE PREFERRED EMBODIMENTS

Figure 1:
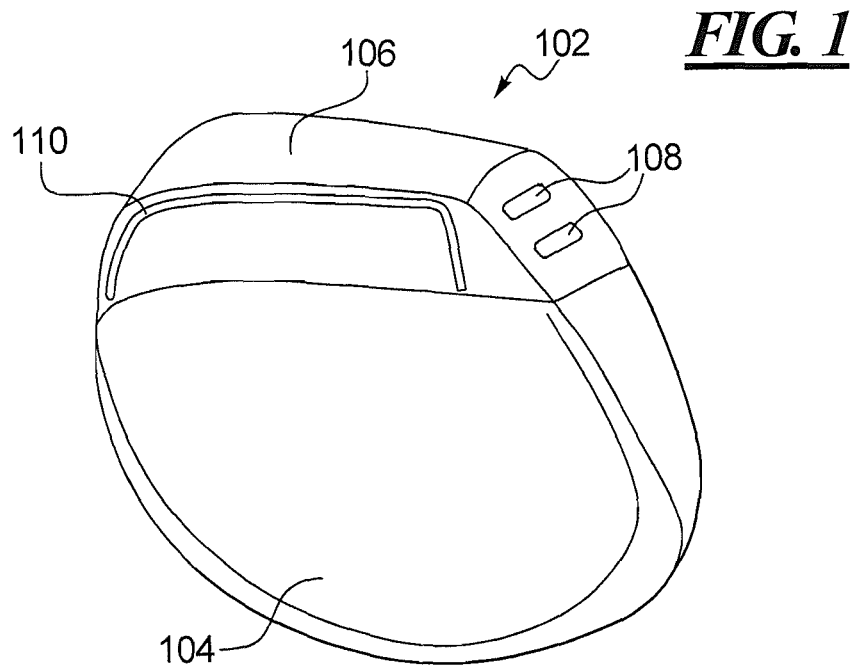
FIG. 1 is a schematic perspective view of an embodiment of an implantable medical device (IMD) of the type used in the apparatus of the invention.

FIG. 1 shows an IMD 102 having a hermetically sealed housing 104 and a connector header 106. The header 106 is provided with lead bores 108 for receiving leads having electrodes to be disposed in operative relation to a patient's heart. The IMD 102 is adapted to be implanted in body tissue. The header 106 is formed from a suitable dielectric material and houses an RF telemetry antenna 110 for wireless communication, which extends along the periphery of the header 106. The housing 104 of the IMD may contain a number of functionally elements and components of the IMD, including a battery, a processor, memory elements and a high voltage output capacitor.

Figure 2:
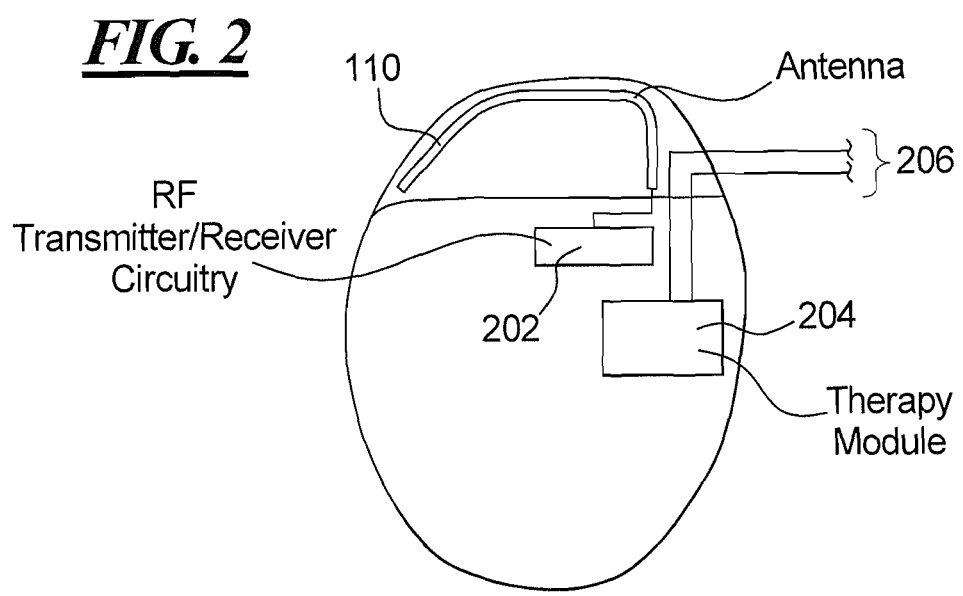
FIG. 2 is a schematic block diagram of certain circuitry components of the IMD of FIG. 1.

FIG. 2 is schematic representation of the IMD 102 of FIG. 1. The housing 104 of the IMD contains RF transmitter/receiver circuitry 202 connected to the antenna 110. The RF transmitter/receiver circuitry 202 and antenna 110 are arranged to wirelessly communicate with an external device comprising transmitter/receiver circuitry and at least one antenna. Further, the housing 104 contains a therapy module 204 which may include electrical devices, microprocessors, controllers, memory elements and power supply. The therapy module 204 is arranged to provide the desired functionality associated with the IMD 102, e.g., defibrillation pulses, pacing simulation and patient monitoring. The therapy module 204 is arranged to be coupled to one or more therapy leads 206.

Figure 3:
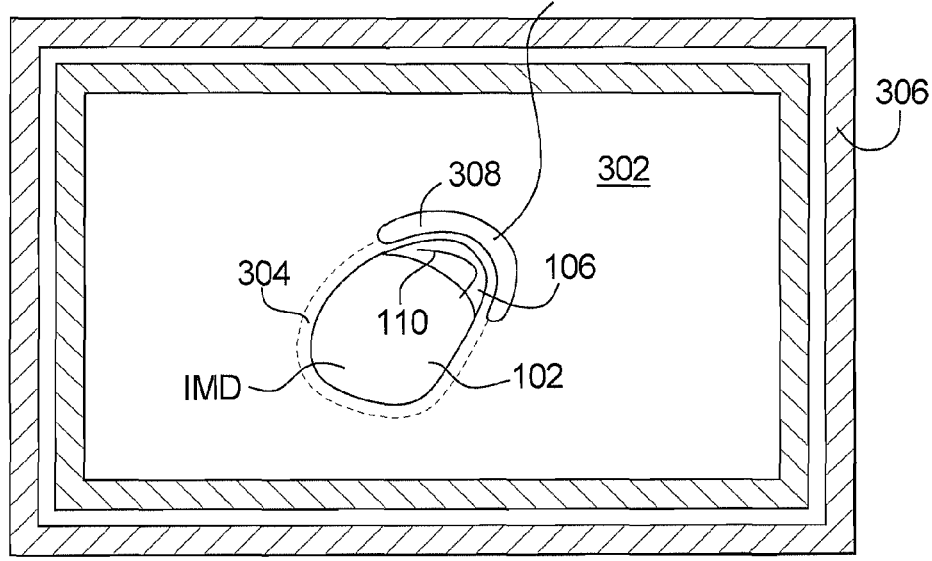
FIG. 3 is a top view of a first embodiment of the apparatus according to the present invention.

FIG. 3 shows a top view of a first embodiment of the apparatus according to the invention. The apparatus comprises an IMD 102 as shown in FIGS. 1 and 2, and a container for storing the IMD 102 prior to implantation in body tissue. The container has a first sealable packaging tray 302 for housing the IMD 102, which first packaging tray 302 has a support in the form of a recess 304 for receiving and supporting the IMD 102. Further, the container has a second sealable packaging tray 306 for housing the first packaging tray 302. The trays 302, 306 are made of a suitable material, such as a rigid plastic material. The seals of the first and second packaging trays 302, 306 are excluded in FIG. 3. The apparatus includes an impedance altering substance in the form of one member 308 positioned in proximity to the IMD 102, when stored in the container, and in proximity to the recess 304. More precisely, the member 308 is positioned in the close surroundings of the antenna 110 and the recess 304 has such a configuration that the antenna 110 of a stored IMD 102 is positioned in close proximity to the member 308. The member 308 extends along a substantial portion of the length of the antenna 110, and along the edge of the header 106, and advantageously, the member 308 abuts the header 106.

Figure 4:
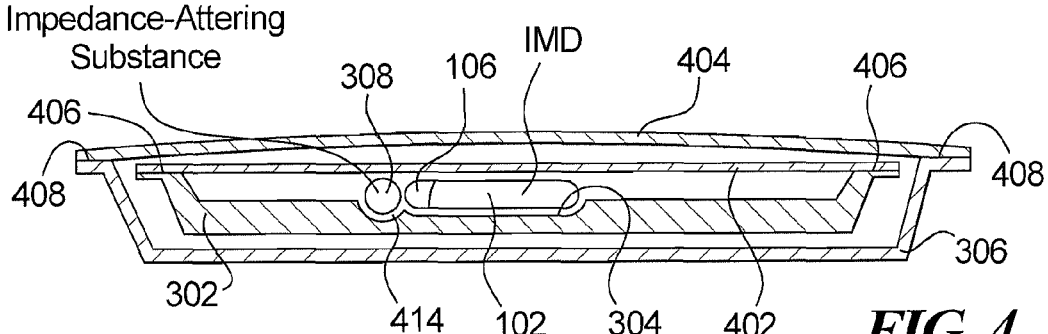
FIG. 4 is a cross-sectional side view of the apparatus of FIG. 3.

FIG. 4 is a cross-sectional side view of the apparatus of FIG. 3. The seal 402 of the first packaging tray 302 and the seal 404 of the second packaging tray 306 are shown in FIG. 4. Each seal 402, 404 is formed by a sheet that is glued to a periphery contact face 406, 408 of respective packaging tray 302, 306. These seals are permeable to a sterilizing gas which is used during the packaging process. The first packaging tray 302 comprises an inner compartment 414 for receiving and retaining the member 308, and the member 308 is thus positioned on the inside of the first packaging tray 302. The member 308 is arranged to mechanically fix the IMD 102 in its position in the first packaging tray 302.

Figure 5:
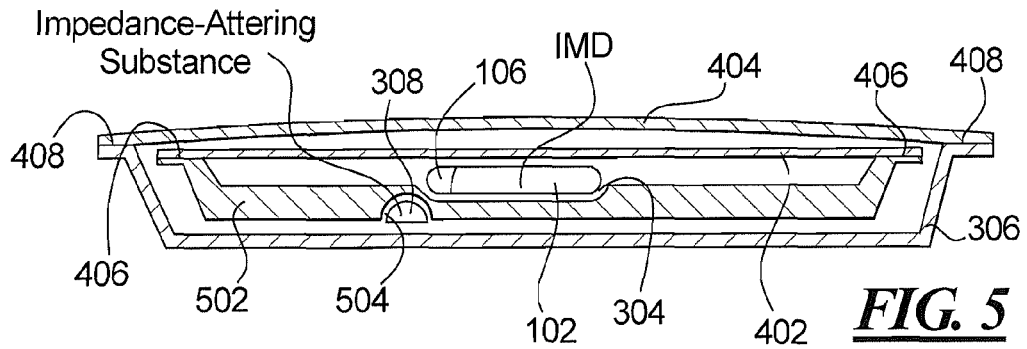
FIG. 5 is a cross-sectional side view of a second embodiment of the apparatus according to the present invention.

FIG. 5 is a cross-sectional side view of a second embodiment of the apparatus according to the present invention, comprising an IMD 102 and a member 308 corresponding to the IMD 102 and the member 308 of the embodiment of FIGS. 3 and 4, but with a different container. Here, the inner packaging tray 502 is provided an external compartment 504 for receiving and retaining the member 308, and the member 308 is thus positioned on the outside of the inner packaging tray 502. This position of the member 308 is advantageous if the member 308 is formed by a bag with gel or liquid. In case the bag is damaged during storage and gel leaves the bag, the gel will not contaminate the IMD 102.

FIG. 6 is a cross-sectional side view of a third embodiment of the apparatus according to the present invention, including an IMD 102 and a member 308 corresponding to the IMD 102 and the member 308 of the embodiment of FIGS. 3 and 4, but with a different container. In this embodiment, the outer packaging tray 602 is provided with an external compartment 604 for receiving and retaining the member 308, and the member 308 is thus positioned on the outside of the outer packaging tray 602. The inner packaging tray 606 is provided with a compartment 608 for receiving the external compartment 604 of the outer packaging tray 602, such that the member 308 is positioned in close proximity to the header 106 of the stored IMD 102. This position of the member 308 is advantageous if the member 308 is formed as a bag with gel or liquid. In case the bag is damaged during storage and gel leaves the bag, the gel will not contaminate the sterilized environment on the inside of the outer packaging tray 602, and thus not contaminate the outside of the inner packaging tray 606.

The member could also be positioned on the outside of the second packaging tray and still be in proximity to the antenna of the IMD.

Since two sealable packaging trays are used, the whole inner tray will be kept sterile during storage, i.e. including the outside of the inner tray and the inside of the outer tray. This is advantageous in the surgical theatre during the implementation process when the IMD will be unpacked.

In the above-mentioned embodiments of the apparatus, the member 308 Is formed as a bag 308 filled with a gel. The dielectric constant and conductivity of the member 308 are set such that the input impedance of the antenna 110 is passively adjusted to improve receive and transmit properties of the antenna 110 when the implantable medical device is stored in the container. The dielectric constant of the member is between 10 and 60, and more precisely between 30 and 40.

By passively altering the electrical material properties of the container in the surroundings of the antenna of the IMD such that they better correspond to the electrical material properties of body tissue, the input impedance of the antenna, when the IMD is stored in the container, corresponds better to the input impedance of the antenna when the IMD is implanted and located in body tissue, whereby the antenna is matched to the transmitter/receiver circuitry of the IMD also when the IMD is stored in the container. The efficiency of the antenna outside the body tissue is thereby improved, and thus the telemetry communication between an external device and an implantable medical device stored prior to implantation is improved.

The invention also relates to a container as described above that embodies such a member.

FIG. 7A is a schematic flow diagram illustrating two embodiments of the method according to the present invention. A first of these embodiments includes the steps of providing an inner packaging tray with a compartment on the inside of the inner packaging tray, at 701, and fixing the above-mentioned bag in the compartment on the inside of said tray, at 702. The inner packaging tray is placed inside an outer packaging tray, at 703. An IMD is placed in a recess formed by the inner packaging tray, at 704, such that bag is positioned in the close surroundings of the antenna and along a substantial portion of the length of the antenna. The IMD is mechanically fixed in its position in the recess by means of the bag, at 705. The inner tray is sealed, at 706, and the outer packaging tray is sealed, at 707, whereby the outer packaging tray fully encloses the inner packaging tray. The interior of outer packaging, including the inner packaging is tray, is sterilized by guiding a sterilizing gas through the permeable seal of the outer and the inner packaging tray, at 708. Finally, the packaging trays are inserted in a box, e.g., a cardboard box.

A second embodiment of the method according to the present invention is shown in FIG. 7B and includes the steps of providing an inner packaging tray with a compartment on the outside of the inner packaging tray, at 801, and fixing the above-mentioned bag in the compartment on the outside of the inner packaging tray, at 802. The inner packaging tray is placed inside an outer packaging tray, at 803. An IMD is placed in a recess formed by the inner packaging tray, at 804, such that bag is positioned in the close surroundings of the antenna and along a substantial portion of the length of the antenna. The following steps 805, 806 and 807 correspond to the above-mentioned steps 706 to 708.

Alternatively, the outer packaging tray is provided with a compartment on the outside of the outer packaging tray, and the bag is fixed in this compartment on the outside of the outer packaging tray.

Naturally, in other embodiments falling within the scope of the claims, some of the above-mentioned steps can be performed in a different order.

Although modifications and changes may be suggested by those skilled in the art, it is the intention of the inventor to embody within the patent warranted heron all changes and modifications as reasonably and properly come within the scope of his contribution to the art.

I claim as my invention:

1. A medical apparatus comprising:
   an implantable medical device comprising transmitter/receiver circuitry and at least one antenna for wireless communication, said antenna having an input impedance configured for an implanted environment;
   a container in which said implantable medical device is stored prior to implantation; and
   an impedance altering substance located in said container in proximity to said implantable medical device in said container and completely out of contact with said antenna, said impedance altering substance having electrical material properties that passively and non-structurally alter the input impedance of the antenna and that set the dielectric constant of a region of the container in proximity to said antenna to a value in said region that corresponds to the implanted environment to improve reception and transmission properties of the antenna when the implantable medical device is in said container.

2. An apparatus as claimed in claim 1 wherein said impedance altering substance is formed as a discrete member that is held in said container.

3. An apparatus as claimed in claim 2 wherein said member is positioned in close proximity to said antenna in said container and out of direct physical contact with said implantable medical device in said container.

4. An apparatus as claimed in claim 3 wherein said member extends along a substantial portion of a length of said antenna in said container.

5. An apparatus as claimed in claim 2 wherein said container comprises a sealable packaging tray having a compartment in which said implantable medical device is received, and wherein said member is located inside of said packaging tray.

6. An apparatus as claimed in claim 5 wherein said member mechanically fixes said implantable medical device in said compartment in said packaging tray.

7. An apparatus as claimed in claim 2 wherein said container comprises a sealable packaging tray having a compartment in which said implantable medical device is received, and wherein said member is located on an exterior of said packaging tray.

8. An apparatus as claimed in claim 2 wherein said container comprises a sealable first packaging tray having a compartment in which said implantable medical device is received, and a sealable second packaging tray in which said first packaging tray is received, and wherein said member is positioned on an exterior of said second packaging tray.

9. An apparatus as claimed in claim 8 wherein said second packaging tray comprises a compartment in which said member is received and held.

10. An apparatus as claimed in claim 2 wherein said member comprises a bag filled with material selected from the group consisting of fluid material and solid material.

11. An apparatus as claimed in claim 2 wherein said member is a unitary, solid component.

12. An apparatus as claimed in claim 2 wherein said member comprises dielectric material.

13. An apparatus as claimed in claim 12 wherein said member comprises dielectric material having a dielectric constant above 10.

14. An apparatus as claimed in claim 12 wherein said member comprises dielectric material having a dielectric constant between 10 and 60.

15. An apparatus as claimed in claim 12 wherein said member comprises dielectric material having a dielectric material having a dielectric constant between 30 and 40.

16. An apparatus as claimed in claim 1 wherein said impedance adjusting substance sets a conductivity in a region of said container in which said antenna is located.

17. A container for storing an implantable medical device having an antenna that has an input impedance, said container comprising:
    a packaging tray configured to receive said implantable medical device therein, said packaging tray comprising a support configured to support said implantable medical device at a position in said packaging tray; and
    an impedance altering substance located in proximity to said support at a location relative to said position that keeps said impedance altering substance completely out of contact with said antenna when said implantable medical device is present in said packaging tray, said impedance altering substance having electrical properties that passively and non-structurally alter the input impedance of the antenna and that set the dielectric constant of a region of the packaging tray in proximity to said antenna to a value that corresponds to the implanted environment to improve reception and transmission properties of the antenna when the implantable medical device is located in the packaging tray.

18. A container as claimed in claim 17 wherein said impedance altering substance is formed as a discrete member that is held in said packaging tray.

19. A container as claimed in claim 18 wherein said member is positioned in close proximity to said antenna in said packaging tray and out of direct physical contact with the implantable medical device when the implantable medical device is located in the packaging tray.

20. A container as claimed in claim 18 wherein said member extends along a substantial portion of a length of said antenna in said packaging tray.

21. A container as claimed in claim 18 wherein said packaging tray is a sealable packaging tray having a compartment in which said implantable medical device is received, and wherein said member is located inside of said packaging tray.

22. A container as claimed in claim 21 wherein said member mechanically fixes said implantable medical device in said compartment in said packaging tray.

23. A container as claimed in claim 18 wherein said packaging tray is a sealable packaging tray having a compartment in which said implantable medical device is received, and wherein said member is located on an exterior of said packaging tray.

24. A container as claimed in claim 18 wherein said packaging tray is formed as a sealable first packaging tray having a compartment in which said implantable medical device is received, and a sealable second packaging tray in which said first packaging tray is received, and wherein said member is positioned on an exterior of said second packaging tray.

25. A container as claimed in claim 24 wherein said second packaging tray comprises a compartment in which said member is received and held.

26. A container as claimed in claim 18 wherein said member comprises a bag filled with material selected from the group consisting of fluid material and solid material.

27. A container as claimed in claim 18 wherein said member is a unitary, solid component.

28. A container as claimed in claim 18 wherein said member comprises dielectric material.

29. A container as claimed in claim 28 wherein said member comprises dielectric material having a dielectric constant above 10.

30. A container as claimed in claim 28 wherein said member comprises dielectric material having a dielectric constant between 10 and 60.

31. A container as claimed in claim 28 wherein said member comprises dielectric material having a dielectric material having a dielectric constant between 30 and 40.

32. A container as claimed in claim 17 wherein said impedance adjusting substance sets a conductivity in a region of said container in which said antenna is located.

33. A method for packaging an implantable medical device prior to implantation, said implantable medical device comprising transmitter/receiver circuitry and at least one wireless antenna for wireless communication, said antenna having an input impedance configured for an implanted environment, said method comprising the steps of:
   placing said implantable medical device in a container;
   also placing an impedance altering substance in said container at a location that keeps said impedance altering substance completely out of contact with the container; and
   forming the impedance altering substance with electrical material properties that set the dielectric constant of a region of the container in proximity to said antenna to a value that corresponds to an implanted environment to improve reception and transmission properties of the antenna while said implantable medical device is in said container.

34. A method as claimed in claim 33 comprising forming said impedance altering substance as a discrete member that is held in said container.

35. A method as claimed in claim 34 comprising positioning said member in close proximity to said antenna in said container and out of direct physical contact with the implantable medical device when the implantable medical device is located in the container.

36. A method as claimed in claim 35 comprising extending said member along a substantial portion of a length of said antenna in said container.

37. A method as claimed in claim 34 comprising forming said container as a sealable packaging tray having a compartment in which said implantable medical device is received, and locating said member is located inside of said packaging tray.

38. A method as claimed in claim 37 comprising using said member to mechanically fix said implantable medical device in said compartment in said packaging tray.

39. A method as claimed in claim 34 comprising forming said container as a sealable packaging tray having a compartment in which said implantable medical device is received, and locating said member on an exterior of said packaging tray.

40. A method as claimed in claim 34 comprising forming said container as a sealable first packaging tray having a compartment in which said implantable medical device is received, and a sealable second packaging tray in which said first packaging tray is received, and positioning said member on an exterior of said second packaging tray.

41. A method as claimed in claim 40 comprising providing said second packaging tray with a compartment in which said member is received and held.

42. A method as claimed in claim 34 comprising forming said member as a bag filled with material selected from the group consisting of fluid material and solid material.

43. A method as claimed in claim 34 comprising forming said member as a unitary, solid component.

44. A method as claimed in claim 34 comprising forming said member from dielectric material.

45. A method as claimed in claim 44 comprising forming said member from dielectric material having a dielectric constant above 10.

46. A method as claimed in claim 44 comprising forming said member from dielectric material having a dielectric constant between 10 and 60.

47. A method as claimed in claim 44 comprising forming said member from dielectric material having a dielectric material having a dielectric constant between 30 and 40.

48. A method as claimed in claim 33 comprising forming said impedance adjusting substance setting a conductivity in a region of said container in which said antenna is located.

* * * * *